US007003355B1

(12) United States Patent
Suaning et al.

(10) Patent No.: US 7,003,355 B1
(45) Date of Patent: Feb. 21, 2006

(54) VISION PROSTHESIS FOR THE BLIND AND METHOD FOR IMPLEMENTING SAME

(76) Inventors: Gregg J. Suaning, 89 Gilda Drive, Narara (AU) NSW 2250; Nigel H. Lovell, 273 Rainbow Street, Coogee (AU) NSW 2034; Yves K. Kerdraon, Sydney Eye Hospital, Sydney (AU) NSW 2000

(*) Notice: Subject to any disclaimer, the term of this patent is extended or adjusted under 35 U.S.C. 154(b) by 377 days.

(21) Appl. No.: 10/300,342

(22) Filed: Nov. 20, 2002

Related U.S. Application Data

(60) Provisional application No. 60/331,579, filed on Nov. 20, 2001.

(51) Int. Cl.
*A61N 1/20* (2006.01)
(52) U.S. Cl. ....................................... 607/54
(58) Field of Classification Search ............. 607/1, 607/53, 54, 116, 148, 149; 623/6.63; 600/558
See application file for complete search history.

(56) References Cited

U.S. PATENT DOCUMENTS

| 5,935,155 A | 8/1999 | Humayun et al. |
| 6,427,087 B1 * | 7/2002 | Chow et al. ................ 607/54 |
| 6,458,157 B1 * | 10/2002 | Suaning ................... 623/6.63 |
| 2002/0038134 A1 * | 3/2002 | Greenberg et al. ............ 607/1 |

* cited by examiner

*Primary Examiner*—George Manuel
(74) *Attorney, Agent, or Firm*—Coats & Bennett, P.L.L.C.

(57) ABSTRACT

The invention described herein comprises an electronic retinal prosthesis for the treatment of some forms of blindness in animals (humans inclusive) wherein surviving retinal neurons of an intact, damaged, or diseased retina, may be physiologically activated by way of electrical stimulation delivered from electrodes placed in biologically sustainable positions so as to produce the perception of light in said animal.

10 Claims, 1 Drawing Sheet

VISION PROSTHESIS FOR THE BLIND AND METHOD FOR IMPLEMENTING SAME

RELATED APPLICATIONS

This application claims priority under U.S.C. §119(e) from provisional application No. 60/331,579 entitled "Vision Prosthesis for the Blind, Sustainable Electrode Positioning and Method for Implementing the Same" filed 20 Nov. 2001.

FIELD OF THE INVENTION

The present invention relates generally to a method and apparatus for treating some forms of blindness, and more particularly to a method and apparatus for stimulating the retina in the eye.

BACKGROUND OF THE INVENTION

The eyes enable light perception in animals. The animal perceives visual images when an eye senses light and sends visual information to the brain via the optic nerve. Each eye includes the sclera, retina, pupil, lens, and a vitreous chamber filled with vitreous humor. The outer layer of the eye includes an opaque portion, the sclera, that is continuous with a transparent portion, the cornea, for receiving light. The iris regulates the light, entering the eye through the cornea, that passes through to the lens. The lens focuses the light through the vitreous chamber and onto a network of neurons and fibers, known as the neural retina, some cells of which (the retinal ganglion cells) collect together to form the optic nerve.

Vision loss and/or blindness results when the neurons in the retina are damaged or destroyed, e.g., by disease. Known prior art efforts for treating this vision loss include electrically stimulating surviving retinal neurons. Passage of electrical current, from one or more stimulating electrode(s), through or across retinal neurons, en-route to a reference electrode or plurality of reference electrodes, results in physiological excitation of said retinal neurons in the form of change in trans-membrane electrical potential of one or more neuronal cells. Said change in trans-membrane electrical potential, if sufficient in magnitude, eventuates, directly or indirectly, the propagation of action potentials along the optic nerve to the vision centers and accessory optic pathways of the brain. Upon receipt of the action potentials by the vision centers and accessory optic pathways, perception of light and other physiological responses occur.

The electrical properties of the eyes have been studied and documented for decades. In a 1956 study, "The Passive Electrical Properties of the Frog's Retina and Sclera for Radial Fields and Currents" (Journal of Physiology, 134: 339–352), Giles Brindley revealed a structure he deemed the "R-Membrane". He described the R-Membrane as, "a retinal structure of high radial resistance and capacity and small thickness." He went on to suggest that the R-Membrane was associated with the external limiting membrane. Subsequent investigators have determined that the R-Membrane is associated with the tight junctions of the retinal pigment epithelium. The results from these investigations are recorded in "Localization of Electrical Activity in the Cat Retina by an Electrode Marking Method," by K. T. Brown and K. T. Tasaki (Journal of Physiology, 1961, 158:281–295), and in "On the R-Membrane in the Frog's Eye: Its Localization and Relation to the Retinal Action Potential," by T. Tomita, M. Jurakami, and Y. Hashimoto (Journal of General Physiology, 1960, 43:81–94). These studies have documented various electrical properties of the retina.

Further, K. T. Brown and T. N. Wiesel disclosed in "Localization of Origins of Electroretinogram Components by Intraretinal Recording in the Intact Cat Eye," (Journal of Physiology, 1961, 158:257–280) that the vitreous humor approximates an isopotential medium, a fact confirmed by the inventors through experimentation. As disclosed in "Trans-Retinal Electrical Stimulation using a Neuroprosthesis: The Effects of Damage to the R-membrane," by G. J. Suaning, N. H. Lovell, and Y. A. Kerdraon (24th Annual International Conference of the IEEE Engineering in Medicine and Biology Society, 23 –26 Oct. 2002, Houston, Tex., USA), moving the location of the intravitreal electrode within the vitreous chamber had no discernable effect on the amplitude of the electrically evoked potential (EEP) measured from the visual cortex of the sheep. In the same study, the recorded EEP was of similar amplitude to the visually evoked potential (VEP) derived by strobe-light stimuli. The similarity in these amplitudes is apparently associated with stimulation of large regions of the neural retina. These observations are not surprising and indeed concur with D. R. Crapper and W. K. Noell's 1963 study, "Retinal Excitation and Inhibition from Direct Electrical Stimulation," (Journal of Neurophysiology, 26:924–947). According to Crapper and Noell, "The high conductivity of the vitreous humor and a high resistance of uniform distribution at the outer retinal surface probably are responsible for the finding that the trans-retinal pulse stimulated a wide retinal area and that electrical stimulation elicited similar phenomena as diffuse light stimulus." The above journal articles are hereby incorporated by reference.

Currently, some prior art methods stimulate the retina by attaching electrodes to the retina. For example, U.S. Pat. No. 5,935,155 to Humayun et al., herein referred to as the Humayun patent, discloses a vision prosthesis that includes an electrode array secured to the retina and stimulating electronics connected to the electrode array. An external camera, and the corresponding electronics, captures and processes images, encodes the resulting data, and transmits the data to the stimulating electronics. The stimulating electronics interpret the received data and activates one or more electrodes in the electrode array to stimulate the retina.

U.S. Pat. No. 6,427,087 to Chow et al., herein referred to as the Chow patent, discloses a vision prosthesis that includes stimulating electrodes and a ground electrode surgically implanted in the eye. The stimulating electrodes contact one side of the retina while the ground electrode passes through the retina and is positioned on the opposite side of the retina from the stimulating electrodes. Generally, the stimulating electrodes consist of photodiodes that detect light entering the eye and produce a stimulating electrical signal corresponding to the light. Because the polarity of the ground electrode in the Chow patent is fixed, the Chow invention delivers only monopolar stimulation (no charge balance).

The Humayun and Chow patents are herein incorporated by reference. While active electrodes attached to the retina, as in the Humayun and Chow patents, will stimulate the retina and produce light perception, studies indicate that electrodes in direct physical contact with the retina may cause irreversible damage to neurons and tissue.

According to a 1998 thesis by R. J. Greenberg at Johns Hopkins University entitled "Analysis of Electrical Stimulation of the Vertebrate Retina—Work Towards a Retinal Prosthesis," placement of a retrobulbar electrode in monopolar stimulation (stimulation behind the eye that occurs with respect to a distant electrode) may be inappropriate owing to the current spread associated with the R-Membrane. While this is apparently the case in a healthy eye, the inventors suggest that in a diseased eye, the passive electrical properties may be rather different or can be made appropriate (through modification with laser, chemical treatment or other appropriate means) to allow for radial current flow thus making trans-retinal stimulation a viable option.

SUMMARY OF THE INVENTION

The present invention is directed to a method and apparatus for producing light perception in an eye comprising a vitreous chamber, a sclera, and a retina. In an exemplary embodiment, a visual prosthesis system includes first and second electrodes spaced from the retina, stimulating electronics connected to the first and second electrodes, and image processing electronics to capture and process images and transmit a corresponding data signal to the stimulating electronics.

In exemplary applications, a physician implants the first electrode, spaced from the retina, at one of first and second locations. Further, a physician implants the second electrode, spaced from the retina, at one of the first and second locations. The physician may also connect the first and second electrodes to the stimulating electronics. The stimulating electronics activates the first and second electrodes to stimulate at least a portion of the retina.

DETAILED DESCRIPTION OF THE INVENTION

Figure 1:
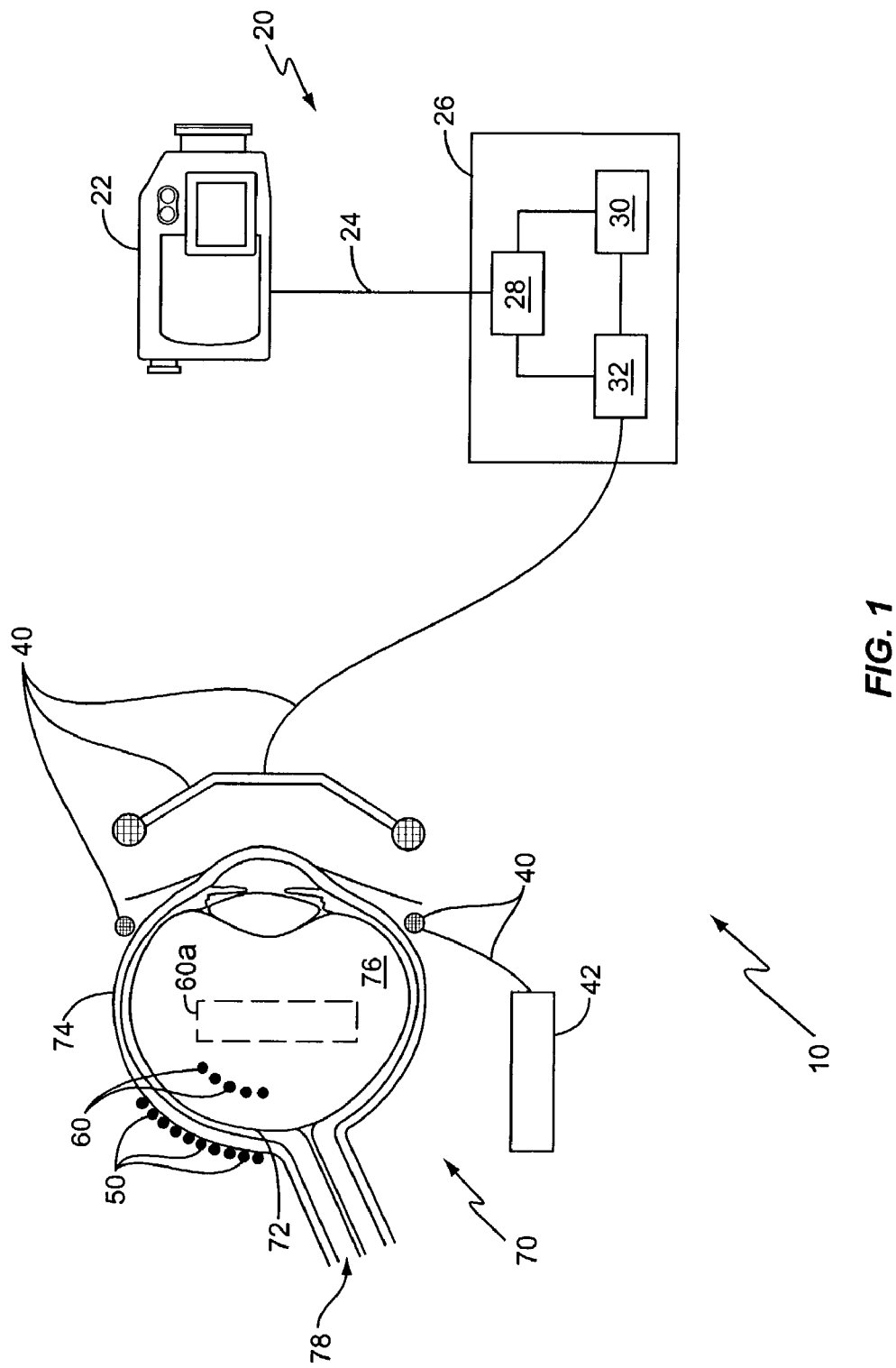
FIG. 1 illustrates an embodiment of a visual prosthesis according to the present invention.

FIG. 1 illustrates a visual prosthesis system, generally indicated by numeral 10, according to the present invention. Visual prosthesis system 10 includes various components, both internal and external to the eye 70 and the patient. Eye 70 includes retina 72, sclera 74, vitreous chamber 76, and optic nerve 78. For simplicity, other areas of the eye such as the cornea, lens, iris, and conjunctiva are not referenced in FIG. 1.

Visual prosthesis system 10 includes imaging electronics 20, data link 40, stimulating electronics 42, stimulating electrodes 50, and reference electrodes 60. The imaging electronics 20 include a camera or other image capture device 22 connected to processing electronics 26 via a data communications line 24. Processing electronics 26 include image processor 28, memory 30, and encoder 32.

In exemplary embodiments, image capture device 22 captures an image from the environment and transfers the image to the image processor 28 within processing electronics 26. Image processor 28 processes the image in any one of numerous ways such as panning, magnification, edge detection, regional averaging, wavelet decomposition, etc., to produce a pixelized abbreviation of the original image. Each pixel of the abbreviated image corresponds to a single or multiple stimulation electrodes 50. Memory 30 stores the processed image.

Upon completion of the formation and storage into memory 30 of the abbreviated image, each of the image's pixels to be conveyed is encoded in encoder 32 according to a pre-determined data transfer protocol for subsequent broadcast across data link 40. Some pixels from the abbreviated image will not be conveyed due to their low level of brightness or other attribute that may render their conveyance inefficient or unnecessary. Data link 40 may be a direct, physical connection of one or more wires conveying both power and data or it may be in the form of inductive or optical coupling, as shown in FIG. 1, so as to avoid the need for wires. The present invention is applicable, but not limited to, the split intraocular-extraocular units as described above. Another embodiment might be a single intraocular device encompassing an image sensor, processor, and stimulating electronics.

Stimulating electronics 42, located either internal to or external from the body, receives and interprets the data transmitted by processing electronics 26 via data link 40. The data contained within the predetermined protocol may include, but is not limited to: information specifying which stimulating electrodes 50 are to be activated with a stimulation pulse, which reference electrodes 60 are to be used as the return path for the stimulation pulse, and the amplitude and pulse width of the stimulation pulse. In the event that a biphasic stimulation pulse is to be delivered, amplitude and pulse width data for each phase of the biphasic stimulation may be directly or indirectly specified. Further, the data may include repetition information that defines the number of times one or more stimulating electrodes 50 are activated with the same stimulating pulse. This repetition may be achieved by way of repeating identical data transmissions or by sending additional data specifying the quantity and frequency of stimulation. The former method is the preferred method as it provides an additional safety mechanism by precluding the possibility of multiple stimulation errors being brought about by a single transmission of corrupt data.

Electronics 42 contains a single or plurality of current sources or sinks that are either multiplexed or directly connected to stimulating or reference electrodes 50, 60 by wires (not shown). The stimulating electronics 42 may execute a variety of functions that are designed to enhance the perception of light in the damaged eye 70. For example, techniques involving steering of current or blocking of particular neuronal regions 72 may be applied to further modulate perception. In addition, variations in stimulus parameters may yield further modulation of perceptions of light. Further, application of blocking currents (anodic blocks, refractory stimulation and the like) may facilitate "steering" particular stimuli to particular and more limited regions of retina 72, and thus further specify perception of light.

The present invention also provides for placing a plurality of stimulating electronics 42 at suitable locations in or near the eye 70. The plurality of stimulating electronics 42 allows for increased quantities of stimulation sites, increased frequency of stimulation, or a combination of both.

Stimulating electrodes 50 and reference electrodes 60, connected to stimulating electronics 42, may be of various sizes and shapes and are positioned at various locations, spaced from the retina 72, on and within the eye 70. Spacing the electrodes 50, 60 from retina 72 avoids unacceptable damage or trauma to the eye 70 and/or orbit (not shown). In exemplary embodiments, electrodes 50, 60 may be in close proximity to the sclerotic coat or sclera 74, a hard, dense and unyielding fibrous membrane that maintains the form of the globe of the eye 70. For example, stimulating electrodes 50 and/or reference electrodes 60 may be wrapped in an envelope of perforated silicone (not shown) and separated from the sclera 74 by approximately 1 mm. Alternatively, electrodes 50, 60 may engage the sclera 74 by attaching to the surface of sclera 74 or by penetrating sclera 74. In this embodiment, the quantity of electrodes 50, 60 is limited only by the surface area of the sclera 74 and the size of each stimulating electrode 50. Other locations for positioning electrodes 50, 60 include, but are not limited to, the vitreous, aqueous, lenticular, iridal, or corneal media, beneath the conjunctiva and in contact with the sclera 74, upon the cornea or beneath the eyelid, and remote to the eye 70 and orbit, e.g., embedded within the temporal bone.

For purposes of illustration, FIG. 1 illustrates stimulating electrodes 50 positioned on the surface of sclera 74, reference electrodes 60 positioned within the vitreous chamber 76, and an optional reference electrode plate 60a positioned on the surface of the sclera 74. It should be noted that the role of the stimulating and reference electrodes 50, 60 may be reversed through electronics, thereby introducing a method of charge balance, which is important for tissue survival. Further, this ability to reverse the role of the electrodes 50, 60 introduces a new configuration wherein electrodes 50, 60 on both sides of the retina 72 may function as either stimulating or reference electrodes 50, 60; neither specifically acts as a ground electrode. Making use of the plurality of locations for both stimulating and reference electrodes 50, 60 in conjunction with reversal of the role of the stimulating and reference electrodes 50, 60, shall facilitate substantial quantities of combinations of current paths and, as a consequence, substantial sites wherein perception of light may be conveyed. The external and internal positioning, with respect to the eye 70, of electrodes 50, 60 makes it feasible to employ a plurality of stimulating electrodes 50. This increases the quantity of electrodes 50 stimulated in parallel, increases the frequency of stimulation (and, as a result, the rate at which the image may be updated), increases the charge injected to a given region, and simultaneously blocks particular neurons or region of neurons with one stimulating electrode 50 by way of application of anodic blockage or other appropriate means of obtaining a refractory state of said particular neurons, while stimulating with another stimulating electrode 50 so as to further modulate perception of light. The positioning allows for a plurality of stimulating electronics 42, as mentioned above, that will allow for all of the above to occur. As a consequence, a plurality of electrodes 50, 60 would also be present.

The following discusses the basic operation of an exemplary embodiment of the present invention. In general, imaging electronics 26 process and encode an image captured by image capturing device 22, and transmit the processed image via data link 40 to stimulating electronics 42, as described above. Electronics 42 analyzes the received data so as to ensure compliance with the pre-determined data transfer protocol and acts upon the data so as to pre-configure the stimulating electronics 42 for the delivery of the specified stimulation event or set of stimulation events to one or more specified stimulating and reference electrodes 50, 60. Subsequent to the appropriate pre-configuration, the actual stimulus is delivered to the specified stimulating electrodes 50. Activating a stimulating pulse that travels from one or more stimulating electrodes 50 positioned upon the sclera 74 to one or more reference electrodes 60 positioned in the vitreous chamber 76 shall pass stimulating current through or across retinal neurons 72. When the stimulation is of sufficient magnitude (current amplitude, pulse duration, injected charge, etc.), perception of light in the region of the stimulated retinal neurons 72 is observed by the individual wearing the invention.

In a non-limiting illustrative example of operation concerning the perception of a point of light with the visual field, stimulating electrode 50 upon sclera 74 is energized by electronics 42 with a cathodic, constant current pulse of programmable amplitude and duration following pre-configuration as described above. Reference electrode 60 may be any one or more of reference electrodes 60 inside or outside of the eye 70 dependent upon the specific nature of visual perception to be delivered to the eye as determined by image processor 28 and encoder 32 based upon the image obtained by image capture device 22. In this instant, the current passes across the scleral tissue 74 and through neuronal layers of the retina 72, causing activation of some of the retinal neurons 72 as it passes. Activation of neurons within the retina 72 leads to perception of light in the vicinity and possibly the surrounding regions of the current path. Following the completion of the first current pulse, a charge recovery pulse may be delivered by the electronics 42. This pulse is of programmable current amplitude and duration and is anodic in polarity with respect to stimulating electrodes 50.

A second non-limiting example illustrates how peripheral vision may be conveyed when gross movement detection is of higher importance than detailed vision. In this instance, reference electrode 60 comprises a reference electrode plate 60a. Reference electrode plate 60a is an external plate, juxtaposed to the periphery of retina 72 and positioned upon sclera 74. Stimulating electrode 50 may be any one or more of electrodes 50, 60 inside or outside of the eye 70, dependent upon the specific nature of the visual perception to be delivered as determined by image processor 28 and encoder 32. With respect to the stimulating electrode 50, cathodic current pulse passes across the tissue of the sclera 74 and through neuronal layers of the retina 72, causing activation of a relatively large region of retinal neurons 72 as it passes through as a consequence of the reference electrode plate 60a, being used as reference electrode. Activation of said neurons 72 leads to perception of light or movement in the vicinity and possibly the surrounding regions of the current path. Following the completion of the first current pulse, a charge recovery pulse may be delivered by the electronics 42. This pulse is of programmable current amplitude and duration and is anodic in polarity with respect to stimulating electrode 50. As a result, reference electrode plate 60a facilitates the physiological activation of large numbers of neurons in the retina 72 at the periphery of the visual field through a single event or a relatively low plurality of events of electrical stimulation thus facilitating the conveyance of gross movement detection at the periphery of the visual field and stimulation of the accessory visual pathways.

In summary, the present invention serves to place electrodes 50, 60 for stimulating the retina 72 in locations whereby biological reactions to the presence of the electrodes 50, 60 are relatively atraumatic to the remaining functions of the eye 70 and orbit not affected by disease. This positioning does not further exacerbate (to significant degree) the effects of disease and facilitates electrical stimulation of neurons 72 not damaged or destroyed by disease. At the same time, the electrode locations facilitate the ability to reliably regionalize electronic stimuli to produce light perception in localized regions of the visual field, and to the accessory optic pathways. In stimulating the accessory optic pathways, mechanisms other than those leading to conscious light perception may notably be elicited (e.g., neurohumoral secretion, ocular reflexes, etc.). In addition to the conveyance of rudimentary light perception through the delivery of stimulus, delivery of successive stimuli to a plurality of electrodes 50, 60 is intended to provide rudimentary patterned vision for use in the conveyance of visual cues, navigation aides, patterns, characters, rudimentary images, and other appropriate visual stimuli.

The foregoing description and drawings describe and illustrate the present invention in detail. However, the foregoing only describes some embodiments of a visual prosthesis system. Accordingly, the present invention may be carried out in specific ways other than those set forth herein without departing from the essential characteristics of the invention. The present embodiments are, therefore, to be considered in all respects as illustrative and not restrictive, and all changes coming within the meaning and equivalency range of the appended claims are intended to be embraced therein.

We claim:

1. A surgical procedure for implanting first and second electrodes in an eye, wherein the eye comprises a vitreous chamber, a retina, and a sclera, the surgical procedure comprising:
   making electrical contact with the sclera by engaging the sclera with the first electrode spaced from the retina;
   implanting the second electrode in the vitreous chamber spaced from the retina, wherein the first and second electrodes are disposed on opposite sides of the retina; and
   stimulating at least a portion of the retina by directing current through the retina between the first and second electrodes.

2. The surgical procedure of claim 1 wherein engaging the sclera with the first electrode comprises engaging the sclera with one of a series of first electrodes and wherein implanting a second electrode comprises implanting one of a series of second electrodes.

3. The surgical procedure of claim 1 further comprising:
   producing a data signal by capturing and processing an image, wherein the data signal comprises at least one electrical signal corresponding to the processed image;
   transmitting the data signal to stimulating electronics connected to the first and second electrodes; and
   activating the first and second electrodes with the data signal.

4. The surgical procedure of claim 3 wherein the data signal further comprises target and repetition information, and wherein activating the first and second electrodes with the data signal comprises applying the at least one electrical signal a specified number of times defined by the repetition information to the first and second electrodes identified by the target information.

5. The surgical procedure of claim 1 wherein engaging the sclera comprises penetrating the sclera with the first electrode.

6. A visual prosthesis for producing light perception in an eye, wherein the eye comprises a vitreous chamber, a sclera, and a retina, the visual prosthesis comprising:
   a first electrode spaced from the retina and engaged with the sclera to make electrical contact with the sclera;
   a second electrode located within the vitreous chamber and spaced from the retina, wherein the first and second electrodes are disposed on opposite sides of the retina;
   stimulating electronics connected to the first and second electrodes, said stimulating electronics configured to direct a current from at least one of the first electrodes, through the retina, to at least one of the second electrodes; and
   imaging electronics comprising:
      an image capturing device to capture images;
      processing electronics to process the captured images and to generate a data signal corresponding to the processed images; and
      transmission electronics to transmit the data signal to the stimulating electronics.

7. The visual prosthesis of claim 6 wherein the first electrode penetrates the sclera.

8. The visual prosthesis of claim 6 wherein the first electrode comprises an external plate.

9. The visual prosthesis of claim 6 wherein the data signal comprises at least one electrical signal corresponding to the processed image.

10. The visual prosthesis of claim 9 wherein the data signal further comprises target and repetition information, and wherein the repetition information specifies the number of times to apply the at least one electrical signal to first and second electrodes identified by the target information.

* * * * *